US006936019B2

United States Patent
Mason

(10) Patent No.: US 6,936,019 B2
(45) Date of Patent: Aug. 30, 2005

(54) STRAP CONNECTOR ASSEMBLY FOR AN ORTHOPEDIC BRACE

(75) Inventor: Jeffrey T. Mason, Escondido, CA (US)

(73) Assignee: Breg, Inc., Vista, CA (US)

( * ) Notice: Subject to any disclaimer, the term of this patent is extended or adjusted under 35 U.S.C. 154(b) by 392 days.

(21) Appl. No.: 10/099,591

(22) Filed: Mar. 14, 2002

(65) Prior Publication Data

US 2003/0176824 A1 Sep. 18, 2003

(51) Int. Cl.[7] .................................................. A61F 5/00
(52) U.S. Cl. ................................ 602/12; 602/5; 602/23; 602/26
(58) Field of Search ........................ 602/5, 6, 12, 26, 602/23, 60; 128/869, 882, 876, 877; 24/300, 301, 302, 459, 460, 265

(56) References Cited

U.S. PATENT DOCUMENTS

| 58,403 | A | | 10/1866 | Goodwin | |
|---|---|---|---|---|---|
| 732,378 | A | | 6/1903 | Schopbach | |
| 1,153,334 | A | * | 9/1915 | Oswald | 24/498 |
| 2,573,866 | A | | 11/1951 | Murphy | 128/80 |
| 3,387,305 | A | | 6/1968 | Shafer | 2/22 |
| 3,581,741 | A | | 6/1971 | Rosman | 128/80 |
| 4,271,999 | A | | 6/1981 | Stravitz | 224/257 |
| 4,660,240 | A | * | 4/1987 | Hutton et al. | 5/669 |
| 4,993,127 | A | | 2/1991 | Mechem et al. | 24/701 |
| 5,572,774 | A | | 11/1996 | Duren | 24/306 |
| 6,550,070 | B2 | * | 4/2003 | Wiegand | 2/421 |
| 2003/0176823 | A1 | * | 9/2003 | Mason | 602/5 |

* cited by examiner

*Primary Examiner*—Henry Bennett
*Assistant Examiner*—Amanda R. Flynn
(74) *Attorney, Agent, or Firm*—Rodney F. Brown

(57) ABSTRACT

A strap connector assembly for an orthopedic brace has a retention post, which has a post cross-sectional dimension, and a chamber, which has a retention aperture. The retention aperture is bounded at least in part by a flexible segment and has an aperture cross-sectional dimension less than the post cross-sectional dimension when the flexible segment is unstressed. However, the aperture cross-sectional dimension is substantially equal to the post cross-sectional dimension when the flexible segment is stressed by the retention post. The retention aperture, flexible segment and retention post cooperatively enable a user to selectively connect or disconnect a strap to or from the orthopedic brace while maintaining the adjustment of the strap.

41 Claims, 4 Drawing Sheets

Fig. 4
Fig. 5
Fig. 6
Fig. 7

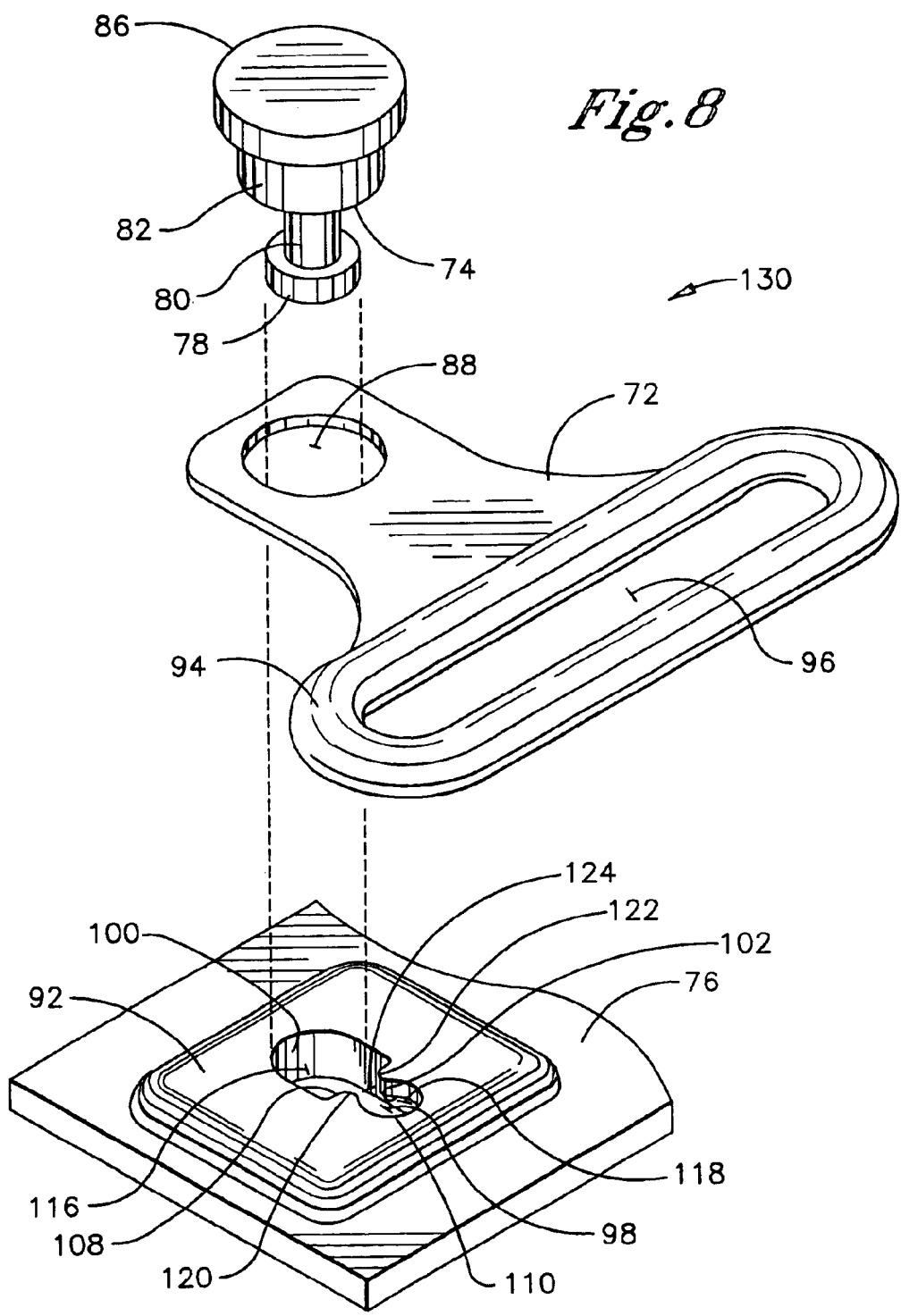

STRAP CONNECTOR ASSEMBLY FOR AN ORTHOPEDIC BRACE

TECHNICAL FIELD

The present invention relates generally to orthopedic braces, and more particularly to a strap connector assembly which enables a user to selectively connect or disconnect a strap to or from an orthopedic brace while maintaining the adjustment of the strap.

BACKGROUND OF THE INVENTION

Conventional orthopedic braces embody a broad range of structures, each having the common purpose of supporting and stabilizing a joint when worn on the body of a user. The orthopedic brace may serve either a preventative role or a remedial role. In a preventative role, the brace provides added support and stability to a healthy skeletal joint, thereby reducing the risk of injury when the joint is subjected to undue stress. In a remedial role, the brace supports and stabilizes a skeletal joint which has been weakened by injury or other infirmity, thereby reinforcing the joint and reducing the risk of further injury to the joint.

Orthopedic braces may be characterized as either soft or rigid. Soft orthopedic braces are composed essentially in their entirety of soft components, i.e., relatively flexible components, such as cloth and flexible foams. An exemplary conventional soft orthopedic brace is a knee brace comprising a support sleeve formed from a stretchable elastic cloth-covered neoprene and one or more flexible, yet relatively non-stretchable, cloth straps partially or fully encircling the support sleeve. The straps may be tightened or loosened by shortening or lengthening the straps, respectively, which enables the user to adjust the fit of the brace to the knee joint and correspondingly to adjust the degree of support the brace provides the knee joint when the support sleeve is positioned over the knee joint.

In contrast to soft orthopedic braces, rigid orthopedic braces include relatively rigid structural components in addition to, or to the exclusion of, soft components. Typically, the rigid structural components of a conventional rigid orthopedic brace are support components dynamically linked together by one or more rotatable hinges enabling controlled pivotal movement of a joint on the body of a user during rehabilitative therapy or user activity. The rigid orthopedic brace is positioned on the body such that the hinges traverse the joint being stabilized, while the rigid components are secured to the body above and below the joint by a plurality of flexible straps which in combination with the rigid components encircle the body.

Referring to FIG. 1, an exemplary prior art rigid orthopedic brace for the knee is shown and generally designated 10. For purposes of illustration, the knee brace 10 is configured for mounting on the right leg. The knee brace 10 comprises medial and lateral hinges 12, 14 and associated medial and lateral condyle pads 16, 18. The medial and lateral hinges 12, 14 pivotally link a pair of rigid upper and lower anterior support cuffs 20, 22 which are shaped to conform to the anterior contours of the upper and lower leg, respectively. The upper anterior cuff 20 is secured in engagement with the upper leg by first and second upper straps 24, 26 which encircle the posterior of the upper leg, while the lower anterior cuff 22 is secured in engagement with the lower leg by first and second lower straps 28, 30 which encircle the posterior of the lower leg. The straps 24, 26, 28, 30 are constructed from a flexible, non-stretchable cloth, such as nylon. Anterior pads 32, 34, 36 are provided to cushion the user's leg from the rigid cuffs 20, 22 and to insure the fit of the knee brace 10 with the leg. The upper anterior pad 32 and lower anterior pads 34, 36 are attached to the upper and lower cuffs 20, 22, respectively, by conventional releasable hook and loop fasteners (not shown), which are commercially available under the trade name "VELCRO".

The cuffs 20, 22 are provided with anterior medial strap retainers 38, 40, 42, 44 which enable connection of the straps 24, 26, 28, 30 to the anterior medial side of the cuffs 20, 22. Although not visible in the view of FIG. 1, it is apparent that anterior lateral strap retainers corresponding to the anterior medial strap retainers 38, 40, 42, 44, respectively, may also be provided, which enable connection of the straps 24, 26, 28, 30 to the anterior lateral side of the cuffs 20, 22. All the strap retainers are substantially identical to one another in construction and function. Accordingly, the following description of the strap retainer 44 applies equally to the remaining strap retainers. The strap retainer 44 is constructed from a material, such as a plastic, which is non-stretchable and substantially more flexible than the rigid cuffs 20, 22, yet substantially more rigid than the flexible straps 24, 26, 28, 30. The configuration of the strap retainer 44 includes a strap loop member 46 having a strap aperture 48 extending through the strap loop member 46, and a body 50 having a mounting aperture 52 extending through the body 50. The strap retainer 44 is substantially permanently rotatably affixed to the lower cuff 22 by a fixed rivet 54 which extends through the mounting aperture 52 and a corresponding opening (not shown) in the lower cuff 22.

The strap 30 has an end 56, which is fitted with a first releasable fastener 58 on one side of the strap 30. The strap 30 correspondingly has a section 60 positioned adjacent to the end 56, which is fitted with a cooperative second releasable fastener 62 on the same side of the strap 30 as the first fastener 58. The first and second fasteners 58, 62 are preferably conventional hook and loop fasteners ("VELCRO"). The strap 30 is connected to the lower cuff 22 by means of the strap retainer 44 and the first and second fasteners 58, 62. In particular, the strap 30 is connected to the lower cuff 22 by threading the end 56 through the strap aperture 48 of the strap loop member 46 and doubling the end 56 back over the section 60 to a point on the section 60 with the first fastener 58 facing the second fastener 62. The first and second fasteners 58, 62 are then pressed against one another to releasably fasten them together. It is apparent that the user is able to adjust the strap 30, specifically, the strap length and strap tension, by selection of the point on the section 60 where the end 56 intersects the section 60.

The strap 30 is disconnected from the lower cuff 22 simply by reversing the above-recited steps for connecting the strap 30 to the lower cuff 22. In particular, the first and second fasteners 58, 62 are separated to release them from one another. The free end 56 is then backed away from the section 60 and out of the strap aperture 48.

Although the above-described prior art structure provides a reliable connection between the flexible straps and rigid cuffs of an orthopedic brace, the structure is not entirely satisfactory with respect to ease of use. In particular, the user must undo the strap adjustment whenever the strap is disconnected from the cuff and redo the strap adjustment (i.e., reset the strap length and tension) whenever the strap is reconnected to the cuff. This procedure becomes time consuming when a plurality of straps are involved as in the case of the present prior art knee brace and/or when the user frequently takes the brace on and off. As such, the present invention recognizes a need for a means of connecting the strap to the cuff of a knee brace which does not require the user to undo and redo the strap adjustment every time the user disconnects and reconnects the strap from and to the cuff. More generally, the present invention recognizes a need for a means of connecting a strap to another component of an orthopedic brace, wherein it is not necessary to undo and redo strap adjustment whenever the strap is disconnected and reconnected from and to the other component of the orthopedic brace.

Accordingly, it is an object of the present invention to provide a strap connector assembly which enables releasable connection or disconnection of a strap to or from another component of an orthopedic brace. It is a further object of the present invention to provide such a strap connector assembly with a strap retainer which engages the strap to achieve a desired adjustment of the strap. It is still a further object of the present invention to provide such a strap retainer which maintains the desired adjustment of the strap whenever the strap is releasably connected or disconnected to or from the other component of the orthopedic brace. These objects and others are accomplished in accordance with the invention described hereafter. Elements of the present invention have also been described in my copending U.S. patent application filed Mar. 14, 2002, entitled "Strap Attachment Assembly for an Orthopedic Brace", incorporated herein by reference.

SUMMARY OF THE INVENTION

The present invention is a strap connector assembly for an orthopedic brace comprising a retention post, which has a post cross-sectional dimension, and a chamber, which has a retention aperture. The retention aperture is bounded at least in part by a flexible segment and has an aperture cross-sectional dimension less than the post cross-sectional dimension when the flexible segment is unstressed. However, the aperture cross-sectional dimension is substantially equal to the post cross-sectional dimension when the flexible segment is stressed by the retention post.

In accordance with one embodiment, the chamber is a first chamber of a plurality of chambers into which a void within a body is segmented. The void is further segmented into a second chamber, wherein the first and second chambers are positioned adjacent one another to form a transition interface between them. The retention aperture is at the transition interface and the flexible segment is a first retention tip bounding a first end of the retention aperture, a second retention tip bounding a second end of the retention aperture, or both the first and second retention tips. The post cross-sectional dimension is the post diameter and the aperture cross-sectional dimension is the separation distance between the first and second retention tips. As such, the separation distance is less than the post diameter when the first or second or both retention tips are unstressed and is substantially equal to the post diameter when the first or second or both retention tips are stressed by the retention post. In addition, the first chamber has a first chamber diameter which is greater than or equal to the post diameter.

In accordance with another embodiment, the above-recited strap connector assembly comprises an anchor and a body which is substantially more flexible than the anchor. The anchor includes a retention post and a retention head positioned atop the retention post. The retention head has a head diameter and the retention post has a post diameter which is less than the head diameter. The body has a void therein which is segmented into a plurality of chambers including a first chamber having a first chamber diameter and a second chamber having a second chamber diameter, which is less than the first chamber diameter. The void may also be segmented into an upper chamber and the first and second chambers, which are positioned below the upper chamber. The upper chamber has an upper diameter greater than or equal to the head diameter.

The first and second chambers are positioned adjacent one another to form a transition interface between them. The first chamber is bounded at least in part by a sidewall and the second chamber is bounded at least in part by a shelf extending inwardly relative to the sidewall. The shelf has an inner surface extending from a first retention tip at one end of the inner surface to a second retention tip at another end of the inner surface, thereby providing a retention aperture at the transition interface. The retention aperture has a separation distance to form a restricted pathway between the first and second chambers. The separation distance is less than the post diameter when the first or second or both retention tips are unstressed and is substantially equal to the post diameter when the first or second or both retention tips are stressed by the retention post. Furthermore, the first chamber diameter is greater than or equal to the head diameter and the second chamber diameter is greater than or equal to the post diameter, but less than the head diameter.

In accordance with yet another preferred embodiment, the anchor is mounted on an orthopedic brace component, which may be a substantially rigid component such as a rigid knee brace cuff, while the body is mounted on a strap retainer having a strap is engaged therewith. The anchor also includes means for fixably mounting the anchor on the orthopedic brace component. In accordance with still another preferred embodiment, the body is mounted on the orthopedic brace component and the anchor is mounted on the strap retainer. In this embodiment, the body includes means for fixably mounting the body on the orthopedic brace component.

The present invention is also a method for connecting a strap to an orthopedic brace employing an embodiment of the above-recited strap connector assembly. As such, the method provides a strap retainer having a body, which includes a chamber having a retention aperture. The retention aperture has an aperture cross-sectional dimension and is bounded at least in part by a flexible segment. The method further provides a retention post which is mounted on an orthopedic brace component. The retention post has a post cross-sectional dimension which is greater than the aperture cross-sectional dimension when the flexible segment is unstressed and substantially equal to the aperture cross-sectional dimension when the flexible segment is stressed by the retention post. The method comprises engaging a strap with the strap retainer and positioning the retention post in the chamber. The retention post is displaced in a first direction away from the chamber into engagement with the flexible segment. The aperture cross-sectional dimension is increased to substantially equal the post cross-sectional dimension by expansion flexion of the flexible segment in response to displacement of the retention post at the post cross-sectional dimension through the retention aperture. The aperture cross-sectional dimension is then decreased to less than the post cross-sectional dimension by elastic retraction of the flexible segment in response to continued displacement of the retention post after the post cross-sectional dimension through the retention aperture. As a result, the retention post resists displacement in a second direction back toward the chamber due to the displacement resistance of the flexible segment and the strap is connected to the orthopedic brace.

The method further comprises disconnecting the strap from the orthopedic brace. The retention post is displaced in the second direction, overcoming the displacement resistance, so that the retention post engages the flexible segment. The aperture cross-sectional dimension is increased to substantially equal the post cross-sectional dimension by expansion flexion of the flexible segment in response to displacement of the retention post at the post cross-sectional dimension through the retention aperture in the second direction. Displacement of the retention post is continued after the post cross-sectional dimension through the retention aperture in the second direction. The retention post is then withdrawn from the chamber.

As an alternative, the above-recited method may be modified by mounting the body on the orthopedic brace component and associating the retention post with the strap retainer. In addition, the present method may further comprise engaging the strap with the strap retainer by initially threading an end of the strap through a strap aperture formed through a strap loop member of the strap retainer. The length of the strap is then selectively fixed at a desired strap adjustment.

In accordance with another embodiment of the present method, the chamber is a first chamber of a plurality of chambers into which a void within a body is segmented. The void is further segmented into a second chamber such that the first and second chambers are positioned adjacent one another to form a transition interface between them. The retention aperture is at the transition interface and the flexible segment is a first retention tip bounding a first end of the retention aperture, a second retention tip bounding a second end of the retention aperture, or both the first and second retention tips. The post cross-sectional dimension is the post diameter and the aperture cross-sectional dimension is the separation distance between the first and second retention tips. As such, the separation distance is less than the post diameter when the first or second or both retention tips are unstressed and is substantially equal to the post diameter when the first or second or both retention tips are stressed by the retention post. In addition, the first chamber has a first chamber diameter which is greater than or equal to the post diameter.

An anchor is provided which includes the retention post and further includes a retention head positioned atop the retention post. The retention head has a head diameter which is greater than the post diameter. The second chamber has a second chamber diameter which is less than the first chamber diameter. The first chamber diameter is greater than or equal to the head diameter and the second chamber diameter is greater than or equal to the post diameter, but less than the head diameter.

The method comprises aligning the first chamber with the retention head and displacing the retention head in a first direction through the first chamber until the retention post is positioned in the first chamber. The retention post is then displaced in a second direction toward the second chamber and into engagement with the first and second retention tips. The separation distance is increased to substantially equal the post diameter by expansion flexion of the first or second or both retention tips in response to displacement of the retention post at the post diameter between the first and second retention tips. Finally, the separation distance is decreased to less than the post diameter by elastic retraction of the first or second or both retention tips in response to continued displacement of the retention post after the post diameter between the first and second retention tips. The retention post is thereby locked into the second chamber, which connects the strap to the orthopedic brace.

The method further comprises disconnecting the strap from the orthopedic brace. The retention post is displaced in a third direction, which is substantially opposite the second direction, toward the first chamber and into engagement with the first and second retention tips. The separation distance is increased to substantially equal the post diameter by expansion flexion of the first or second or both retention tips in response to displacement of the retention post at the post diameter between the first and second retention tips. Displacement of the retention post is continued in the third direction after displacement of the post diameter between the first and second retention tips until the entirety of the retention post is positioned in the first chamber. Finally, the retention head is displaced in a fourth direction, which is substantially opposite the first direction, until the retention head substantially clears the void. The retention post is thereby withdrawn from the void which disconnects the strap from the orthopedic brace without substantially modifying the desired strap adjustment.

The present invention will be further understood from the drawings and the following detailed description.

BRIEF DESCRIPTION OF THE DRAWINGS

FIG. 4 is a bottom view of the body of the strap retainer of FIG. 2.

FIG. 5 is a top view of the body of the strap retainer of FIG. 2.

FIG. 6 is a cross-sectional plan view of the mounted anchor and the body of the strap retainer of FIG. 2, wherein the body engages the anchor such that the strap connector assembly is in an unlocked condition.

FIG. 7 is a cross-sectional plan view of the mounted anchor and the body of the strap retainer of FIG. 2, wherein the body engages the anchor such that the strap connector assembly is in a locked condition.

FIG. 8 is an exploded perspective view of an alternate embodiment of the strap connector assembly of the present invention.

DESCRIPTION OF PREFERRED EMBODIMENTS

Figure 1:
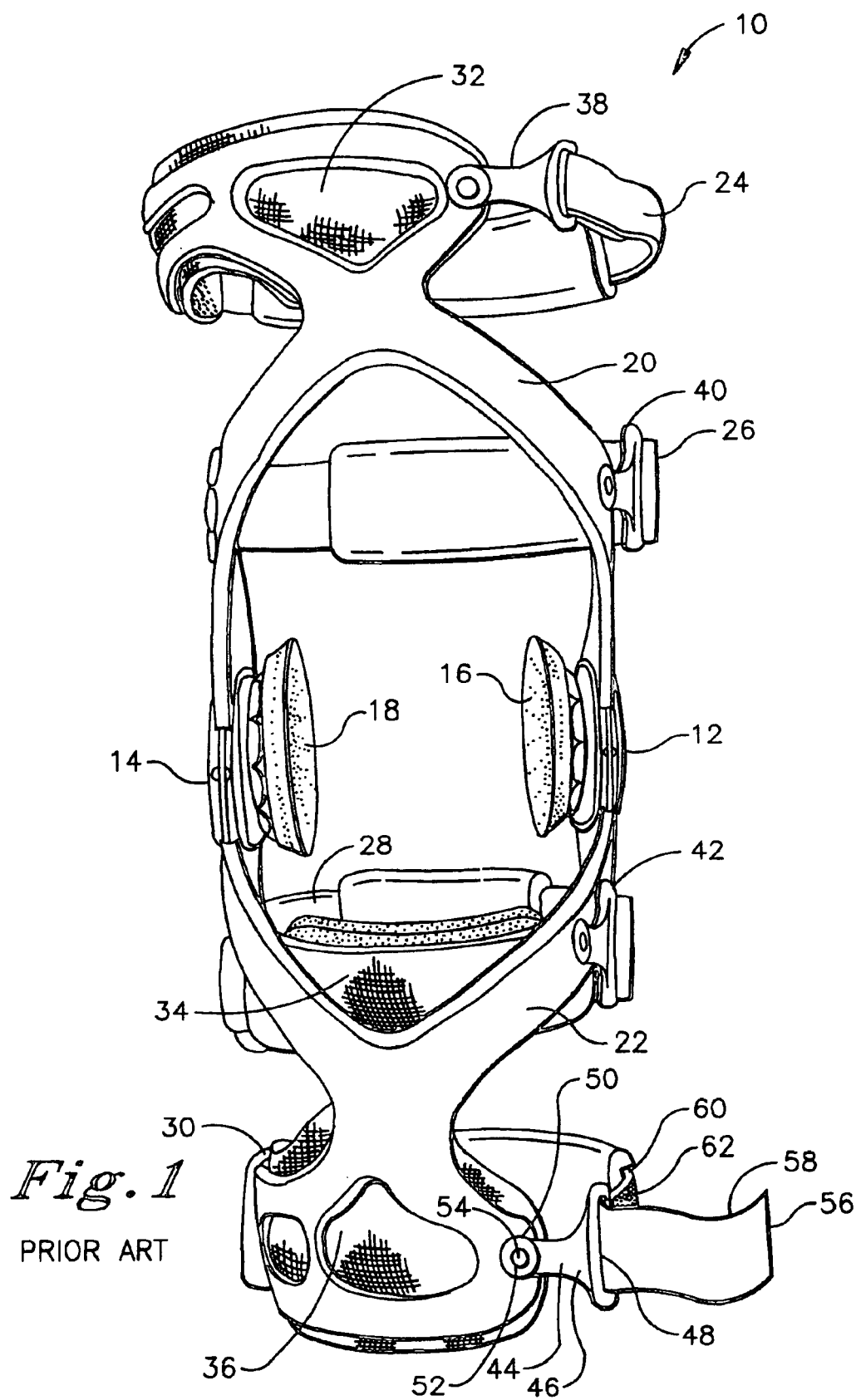
FIG. 1 is a perspective view of a prior art rigid orthopedic knee brace.
Figures 2, 3:
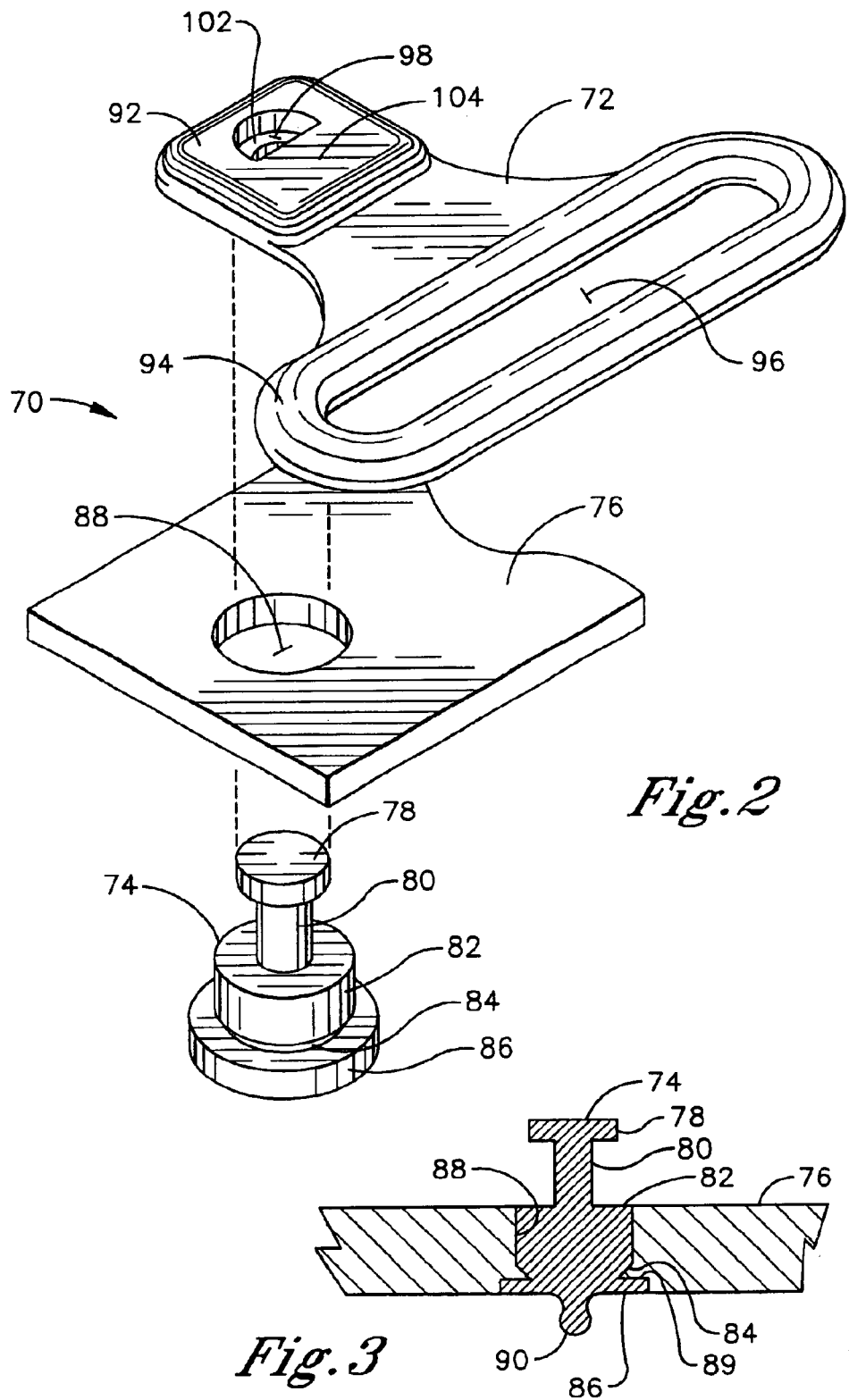
FIG. 2 is an exploded perspective view of a strap connector assembly of the present invention, which includes a strap retainer and anchor, shown in association with an orthopedic brace component.
FIG. 3 is a cross-sectional plan view of the anchor of FIG. 2 fixably mounted on the orthopedic brace component.

Referring to FIG. 2, a strap connector assembly of the present invention is shown and generally designated 70. The strap connector assembly 70 comprises in combination a strap retainer 72 and an anchor 74. The strap retainer 72 and anchor 74 are cooperatively configured in a manner described hereafter to enable rapid and reliable connection of the strap retainer 72 to the anchor 74 and rapid and reliable disconnection of the strap retainer 72 from the anchor 74. The anchor 74 is fixably mountable on an orthopedic brace component 76, which is shown only partially herein. The orthopedic brace component 76 may be any one of the multiple components of a conventional orthopedic brace and is preferably a support member or a hinge. For example, the orthopedic brace component 76 may be the rigid support cuff of a rigid knee brace, as shown in FIG. 1, or the flexible support sleeve of a soft knee brace, as described above.

The anchor 74 is a rigid member preferably fabricated as an integral form from a high-strength material such as steel. The anchor 74 is configured in a series of dimensionally distinct sections, which include, from top to bottom, a retention head 78, a retention post 80, a mounting post 82, a mounting notch 84, and a mounting base 86. Referring additionally to FIG. 3, the retention head 78, retention post 80, mounting post 82, and mounting notch 84 are all sized to fit through a continuous anchor opening 88 extending through the entire thickness of the orthopedic brace component 76. As such, the retention head 78 and retention post 80 each has a diameter substantially less than that of the anchor opening 88. The mounting post 82 has a diameter essentially equal to the diameter of the anchor opening 88 and the mounting base 86 has a diameter substantially greater than that of the anchor opening 88. It is further noted that the retention head 78 has a diameter substantially greater than that of the retention post 80 and less than or equal to that of the mounting post 82.

The anchor 74 is fixably mounted to the orthopedic brace component 76 by press fitting the anchor 74 though the bottom of the anchor opening 88 until the mounting post 82 and mounting base 86 are essentially Flush with the top and bottom of the anchor opening 88, respectively. Specifically, the retention head 78 and retention post 80 are displaced upwardly through the anchor opening 88 so that the mounting post 82 engages the sidewall of the anchor opening 88. The mounting post 82 is pressed upwardly into the anchor opening 88 so that the mounting base 86 engages the bottom edge 89 of the anchor opening 88. The mounting base 86 is then pressed upwardly into the anchor opening 88 with sufficient force to deform and displace the bottom edge 89 of the anchor opening 88 into the mounting notch 84, which fixably retains the anchor 74 in the anchor opening 88 thereafter. The anchor 74 further comprises a male snap member 90 extending from the bottom of the mounting base 86, which has a pad retaining function as described below.

It is understood that other alternate configurations of the anchor and techniques for mounting the anchor on the orthopedic brace component not shown or described in detail herein are possible within the scope of the present invention. For example, the anchor can be mounted on the orthopedic brace component by alternate techniques such as threading, crimping, bonding, welding, fastening, sewing or other techniques known to the skilled artisan. Alternate configurations of the anchor suitable for practice of the present invention provide a retention post 80 and alternate means within the purview of the skilled artisan for mounting the retention post on the orthopedic brace component other than the above-described mounting aperture 52, mounting post 82, mounting notch 84 and mounting base 86. Alternate configurations of the anchor also preferably (but optionally) provide a retention head 78. The optional retention head 78, retention post 80 and orthopedic brace component 76 are oriented to one another as shown in FIG. 3 such that the plane of the retention head 78 extends above the plane of the orthopedic brace component 76 a distance, which essentially corresponds to the length of the retention post 80. In addition, the longitudinal axis of the retention post 80 is oriented essentially perpendicular to the plane of the retention head 78 and the plane of the orthopedic brace component 76.

Referring to FIG. 2, the strap retainer 72 is preferably an element constructed from a high-strength, relatively flexible material such as a plastic. The strap retainer 72 is preferably fabricated as an integral form by means such as conventionally molding the material of choice, e.g., plastic. Thus, the material of the strap retainer 72 and the resulting strap retainer 72 itself are typically substantially more flexible than the material of the anchor 74 and the anchor 74 itself. The strap retainer 72 includes a body 92 and a strap loop member 94. The strap loop member 94 is essentially identical to the strap loop member 46 of FIG. 1. The strap loop member 94 has a strap aperture 96 extending through the strap loop member 94, which enables engagement of an orthopedic brace strap (not shown in FIG. 2) with the strap loop member 94 at a desired strap adjustment in substantially the same manner as described above with respect to FIG. 1.

Figures 4, 5, 6, 7:
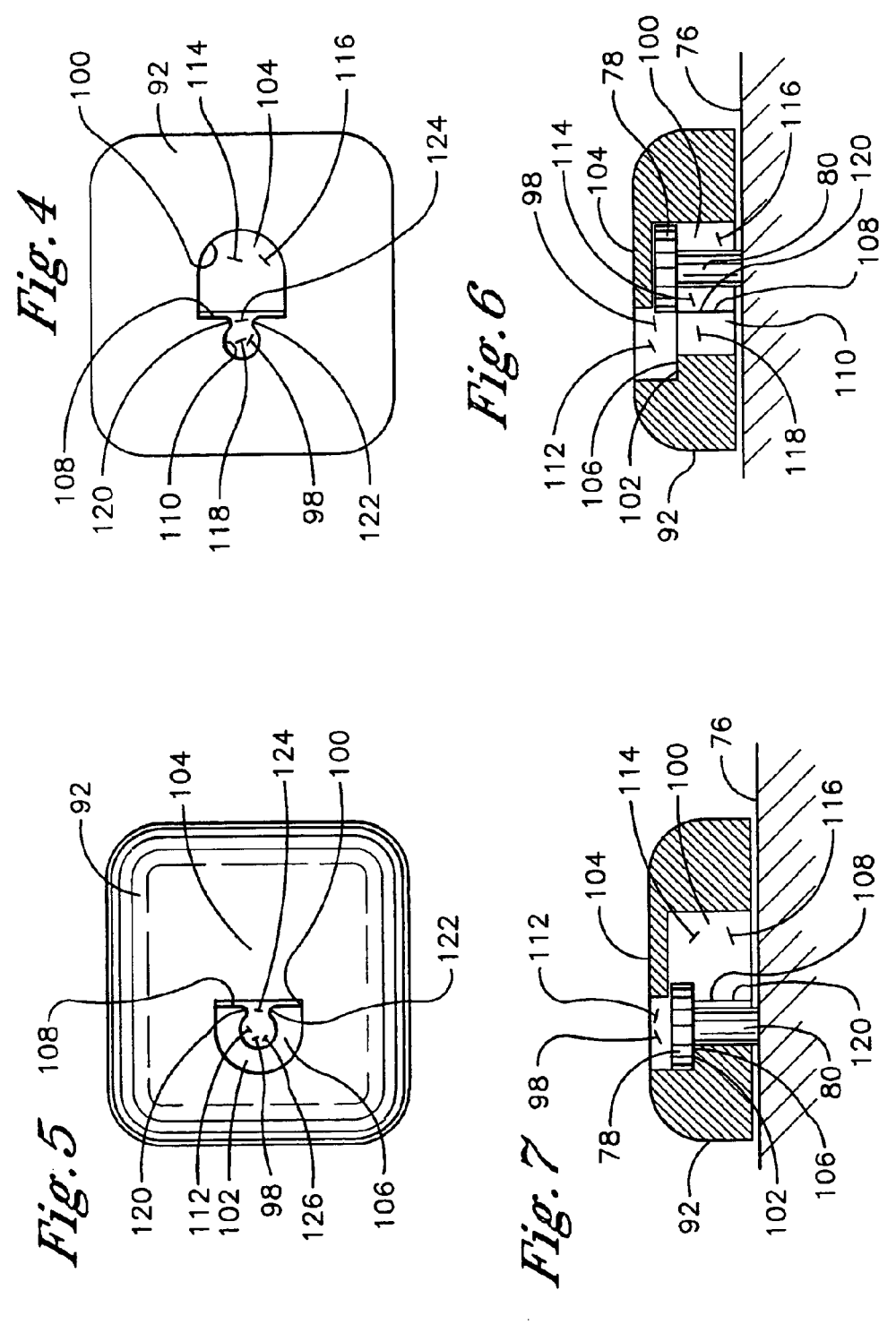

Referring additionally to FIGS. 4 and 5, the body 92 of the strap retainer 72 has a void 98 therein, which is configured to receive and releasably retain the anchor 74 within the void 98. The void 98 is bounded by an interior sidewall 100, an interior shelf 102 extending inwardly relative to the interior sidewall 100, and a partial cover 104 partially extending over the top of the void 98. Alternatively, although not shown, the top of the void 98 may be entirely covered by a full cover rather than the partial cover 104 or entirely uncovered by omitting the partial cover 104 altogether in a manner readily apparent to the skilled artisan. The shelf 102 has a top surface 106, a front surface 108 and an inner surface 110, wherein the top surface 106 is oriented essentially at right angles to the interior sidewall 100. The front surface 108 and inner surface 110 are oriented essentially at right angles to the top surface 106.

The void 98 is segmented, both vertically and horizontally, into a plurality of interconnected chambers. It is noted that the terms "vertical" and "horizontal", as well as the terms "upper" and "lower", are used herein to denote the spatial orientation of the elements of the strap connector assembly 70 relative to one another as displayed in FIG. 2. The terms do not necessarily reflect the spatial orientation of the elements in absolute terms with respect to the external environment when the strap connector assembly 70 is in a preferred operational orientation.

The void 98 is vertically segmented into an upper chamber 112 and a lower chamber 114, wherein the lower chamber 114 is positioned directly beneath the upper chamber 112. The lower chamber 114 is horizontally segmented into a first chamber 116 and a second chamber 118, which are positioned horizontally adjacent to one another. An alternate embodiment of the void 98 not shown eliminates the upper chamber 112 altogether from the void 98. In accordance with this embodiment, the void 98 is only horizontally segmented into the first chamber 116 and the second chamber 118, wherein the tops of the first and second chambers 116, 118 are open to the environment to fully expose the side and top of the retention head 78 during operation of the strap connector assembly 70 described below. As is apparent to the skilled artisan, omission of the upper chamber 112 from the void 98 does not substantially alter the basic function of the body 92.

The upper and first chambers 112, 116 are both horizontally bounded in part by the interior sidewall 100 and the first chamber 116 is vertically continuous with the upper chamber 112. The inner surface 110 of the interior shelf 102 follows a horseshoe-shaped path from a flexible first retention tip, 120 at one end of the inner surface 110 to a flexible second retention tip 122 at the other end of the inner surface 110. The inner surface 110 partially encircles the second chamber 118, thereby defining in part the horizontal boundary of the second chamber 118. The second chamber 118 has a substantially smaller diameter than that of the first chamber 116, wherein the diameter of a non-circular shape is defined herein as the diameter of the smallest circle enclosing (or the largest circle fitting within) the non-circular shape.

The front surface 108 and an opening, where the discontinuous front surface 108 intersects the inner surface 110, which is termed the retention aperture 124, define a substantially planar transition interface between the first and second chambers 116, 118. The retention aperture 124 is bounded at its ends by the first and second retention tips 120, 122, respectively. The retention aperture 124 provides a pathway between the first chamber 116 and the second chamber 118, which is restricted by the first and second retention tips 120, 122. The top surface 106 and an opening in the discontinuous top surface 106, termed the shelf opening 126, define a substantially planar transition interface between the upper and second chambers 112, 118.

Referring additionally to FIGS. 6 and 7, the relative dimensions of the body 92 and anchor 74 enable the desired function of the strap connector assembly 70. In particular, the diameter of the retention head 78 is less than or equal to the diameter of the first chamber 116. The length of the retention aperture 124, i.e., the separation distance between the first and second retention tips 120, 122, is slightly less than the diameter of the retention post 80 when the first and second retention tips 120, 122 are unstressed. The diameter of the second chamber 118 is equal to or slightly greater than the diameter of the retention post 80 and less than the diameter of the retention head 78. The length of the second chamber 118, i.e., the distance from the retention aperture 124 to the closed end of the second chamber 118, is at least greater than the radius of the retention post 80 and preferably equal to or greater than the diameter of the retention post 80. The distance from the top surface 106 of the interior shelf 102 to the bottom of the body 92 is equal to or slightly greater than the distance from the top surface of the orthopedic brace component 76 to the bottom of the retention head 78, which generally corresponds to the height of the retention post 80. The distance from the top surface 106 of the shelf 102 to the bottom of the partial cover 104 or the top of the upper chamber 112 is equal to or greater than the thickness of the retention head 78.

Method of Operation

Operation of the strap connector assembly 70 is described hereafter with reference to FIGS. 6 and 7. To connect the body 92 to the anchor 74 (and correspondingly to connect a strap engaging the strap retainer to an orthopedic brace component), the body 92 is positioned over the anchor 74 such that the first chamber 116 is aligned with the retention head 78. The body 92 is manually lowered onto the anchor 74 with the retention head 78 passing through the first chamber 116 into the upper chamber 112, while the retention post 80 remains in the first chamber 116. Engagement of the bottom of the body 92 with the top surface of the orthopedic component 76 or engagement of the top of the retention head 78 with the bottom of the partial cover 104 functions as a stop against further downward displacement of the body 92 onto the anchor 74. When downward displacement of the body 92 onto the anchor 74 is completed, the retention head 78 resides in the upper chamber 112 with the bottom of the retention head 78 substantially even with or above the top surface 106 of the interior shelf 102. At this point, as shown in FIG. 6, the strap connector assembly 70 is in an unlocked condition. The unlocked condition is so termed because the anchor 74 is received within the void 98 of the body 92, but is not "locked" therein, i.e., the anchor 74 is freely removable from the void 98 with a negligible manual displacement force which is substantially equal to the force of gravity.

The strap connector assembly 70 is transitioned to a locked condition thereafter by manually displacing the anchor 74 in the direction of the second chamber 118 so that the first and second retention tips 120, 122 flexibly engage the opposite sides of the retention post 80, while the retention head 78 remains in the upper chamber 112. Since the distance between the first and second retention tips 120, 122, is slightly less than the diameter of the retention post 80, the first and second retention tips 120, 122 become stressed by the manual displacement force. The first and second retention tips 120, 122 are flexed apart to increase their separation distance as progressively wider vertical cross-sections of the retention post 80 are displaced between the first and second retention tips 120, 122 Ultimately, the first and second retention tips 120, 122 are flexed such that their separation distance is substantially equal to the diameter of the retention post 80 when the full diameter vertical cross-section of the retention post 80, i.e., the widest vertical cross-section of the retention post 80, is positioned between the first and second retention tips 120, 122.

Since the length of the second chamber 118 is at least greater than the radius of the retention post 80, the vertical cross-sections of the retention post 80 passing through the retention aperture 124 become successively narrower with additional horizontal displacement of the retention post 80 into the second chamber 118 after the full diameter vertical cross-section of the retention post 80 has passed through the retention aperture 124. As a consequence the first and second retention tips 120, 122 elastically close toward one another and the separation distance of the first and second retention tips 120, 122 likewise becomes successively narrower, approaching its original unstressed value, with additional horizontal displacement of the retention post 80 into the second chamber 118. It is noted that the bottom of the retention head 78 is positioned immediately above the top surface 106 of the interior shelf 102 for the duration of horizontal displacement of the anchor 74. The bottom of the retention head 78 may be in slidable engagement with the top surface 106 or in non-contact proximity to the top surface 106 depending on the relative dimensions of the anchor 74 and body 92.

If the length of the second chamber 118 is equal to or greater than the diameter of the retention post 80, the entire retention post 80 resides within the second chamber 118 when horizontal displacement of the retention post 80 is terminated against the closed end of the second chamber 118. Even if the length of the second chamber 118 is less than the diameter of the retention post 80, but greater than the radius, the full diameter vertical cross-section of the retention post 80 nevertheless resides within the second chamber 118 when horizontal displacement of the retention post 80 is terminated against the closed end of the second chamber 118. In either case, the retention head 78 resides within the upper chamber 112 above the top surface 106 when horizontal displacement of the retention post 80 is terminated.

The final effect of horizontally displacing the retention post 80 into the second chamber 118 is to transition the strap connector assembly 70 to the locked condition as shown in FIG. 7. The locked condition is so termed because the anchor 74 is essentially "locked" into engagement with the body 92 once horizontal displacement of the retention post 80 into the second chamber 118 is completed so that the body 92 is connected to the anchor 74 (and correspondingly the strap engaging the strap retainer is connected to the orthopedic brace component). Once in the locked condition, the anchor 74 is only disconnected from the body 92 by applying a relatively substantial manual displacement force to the anchor 74 and/or the body 92. In particular, the displacement force must be sufficient to overcome the resistance of the first and second retention tips 120, 122 to flexion. Application of a sufficient displacement force expands the separation distance of the first and second retention tips 120, 122 to a value substantially equal to the diameter of the retention post 80 and permits the retention post 80 to pass through the retention aperture 124 from the second chamber 118 into the first chamber 116.

The anchor 74 is disconnected from the body 92 (and correspondingly the strap engaging the strap retainer is disconnected from the orthopedic brace component) by reversing the above-recited operational steps. Specifically, the anchor 74 is manually displaced horizontally in the direction of the first chambers 116 with a sufficient manual displacement force to expand the separation distance of the first and second retention tips 120, 122 to a value substantially equal to the diameter of the retention post 80. Consequently, the retention post 80 passes through the retention aperture 124 from the second chamber 118 into the first chamber 116 and the head 72 clears the top surface 106 of the interior shelf 102. The anchor 74 is then freely removable from the void 98 by displacing the body 92 upward with a negligible manual displacement force until the anchor 74 clears the void 98.

As is apparent, the strap connector assembly 70 enables rapid connection and disconnection of the anchor to and from the body (and correspondingly of the strap to and from the orthopedic brace component) while maintaining the desired strap adjustment. In other words connection and disconnection of the anchor to and from the body does not require the user to disengage the strap from the strap retainer. Connection and disconnection of the anchor to and from the body can proceed while the strap remains engaged with the strap retainer. The strap connector assembly 70 also enables retention of a pad such as shown in FIG. 1 in releasable engagement with the orthopedic brace component 76. The male snap member 90 (shown in FIG. 3), which extends from the opposite side of the orthopedic brace component 76 as the retention head 78 and retention post 80, is releasably coupled with a conventional female snap member (not shown) positioned on the surface of the pad by forcibly inserting the male snap member 90 into the female snap member. The resulting coupling retains the pad in engagement with the orthopedic brace component 76. The pad is released from engagement with the orthopedic brace component 76 simply by forcibly withdrawing the male snap member 90 from the female snap member.

In accordance with the present embodiment of the strap connector assembly 70, as described above, the anchor 74 is mounted on the orthopedic brace component 76 and the body 92 is mounted on the strap retainer 72. It is further within the scope of the present invention to reverse the relation of the anchor and the body to the orthopedic brace component and the strap retainer, respectively. Referring to FIG. 8, such an alternate embodiment of the strap connector assembly is shown and generally designated 130, wherein components of the strap connector assembly 130 which are common to the strap connector assembly 70 are designated by the same reference characters. As such, the body 92 of the strap connector assembly 130 is mounted on the orthopedic brace component 76 and the anchor 74 of the orthopedic strap connector 130 is mounted on the strap retainer 72. It is understood that the term "mounted on" as used herein is broadly inclusive and encompasses elements which are integral with one another, attached to one another, fastened to one another, or are otherwise connected to one another either directly or indirectly. However, the term "mounted on" is not inclusive of releasable retention of the anchor 74 within the void 98 as described above.

While the forgoing preferred embodiments of the invention have been described and shown, it is understood that alternatives and modifications, such as those suggested and others, may be made thereto and fall within the scope of the invention. In its broadest sense, the present invention encompasses a strap connector assembly having a retention post and a chamber with a retention aperture bounded at least in part by a flexible segment. The retention aperture has a cross-sectional dimension which is less than a cross-sectional dimension of the retention post when the flexible segment is unstressed. However, the aperture cross-sectional dimension is substantially equal to the post cross-sectional dimension when the flexible segment is stressed by the retention post. Thus, the flexible segment provides an interference fit of the retention post through the retention aperture in a first direction, which enables a user to selectively connect a strap to an orthopedic brace by passing the retention post through the retention aperture in the first direction. The flexible segment also provides an interference fit of the retention post through the retention aperture in a second direction, which is substantially opposite the first direction, thereby enabling the user to selectively disconnect the strap from the orthopedic brace by passing the retention post through the retention aperture in the second direction.

I claim:

1. A strap connector assembly for an orthopedic brace comprising:
   a retention post having a post cross-sectional dimension; and
   a chamber having an interior and a peripheral boundary of said interior defined by an inner surface and a retention aperture, wherein said retention aperture is a discontinuity in said inner surface bounded at least in part by a flexible segment of said inner surface, further wherein said retention aperture provides a pathway through said peripheral boundary into or out of said interior of said chamber, and further wherein said retention aperture has an aperture cross-sectional dimension less than said post cross-sectional dimension when said flexible segment is unstressed and substantially equal to said post cross-sectional dimension when said flexible segment is stressed by said retention post and said chamber has a chamber diameter greater than or equal to said post cross-sectional dimension.

2. The strap connector assembly of claim 1 wherein said chamber is a second chamber and said chamber diameter is a second chamber diameter, and wherein said strap connector assembly further comprises a first chamber positioned adjacent said second chamber.

3. The strap connector assembly of claim 2 wherein said first chamber has a first chamber diameter and wherein said first chamber diameter is greater than said second chamber diameter.

4. The strap connector assembly of claim 2 wherein said retention aperture is at a transition interface between said first and second chambers.

5. The strap connector assembly of claim 2 wherein said first chamber is bounded at least in part by a sidewall to define a first chamber diameter and a said inner surface of said second chamber is a surface of a shelf extending inwardly relative to said sidewall to define said second chamber diameter, further wherein said first chamber diameter is greater than said second chamber diameter.

6. The strap connector assembly of claim 2 further comprising a retention head positioned atop said retention post, said retention head having a head cross-sectional dimension greater than said post cross-sectional dimension.

7. The strap connector assembly of claim 6 wherein said second chamber diameter is less than said head cross-sectional dimension.

8. The strap connector assembly of claim 6 wherein said first chamber diameter is greater than said head cross-sectional dimension.

9. The strap connector assembly of claim 1 wherein said post cross-sectional dimension is a post diameter of said retention post.

10. The strap connector assembly of claim 1 wherein said aperture cross-sectional dimension is a separation distance between a first end of said retention aperture and a second end of said retention aperture.

11. The strap connector assembly of claim 10 wherein said flexible segment is a first retention tip at said first end of said retention aperture.

12. The strap connector assembly of claim 11 wherein said flexible segment is a second retention tip at said second end of said retention aperture.

13. A strap connector assembly for an orthopedic brace comprising:
   a retention post having a post diameter; and
   a body including a void segmented into a first chamber and a second chamber positioned adjacent one another to form a transition interface between said first and second chambers, a retention aperture at said transition interface bounded by a first retention tip at a first end of said retention aperture and a second retention tip at a second end of said retention aperture, said first and second retention tips separated by a separation distance, wherein said first chamber has a first chamber diameter greater than or equal to said post diameter and said separation distance is less than said post diameter when said first or second or both retention tips are unstressed and is substantially equal to said post diameter when said first or second or both retention tips are stressed by said retention post.

14. The strap connector assembly of claim 13 wherein said void is bounded by a sidewall bounding said first chamber at least in part to define said first chamber diameter and a shelf extending inwardly relative to said sidewall having an inner surface bounding said second chamber at least in part to define a second chamber diameter, further wherein said first chamber diameter is greater than said second chamber diameter.

15. The strap connector assembly of claim 13 further comprising a retention head positioned atop said retention post, said retention head having a head diameter greater than said post diameter.

16. The strap connector assembly of claim 15 wherein said second chamber has a second chamber diameter greater than or equal to said post diameter and less than said head diameter.

17. The strap connector assembly of claim 13 wherein said second chamber has a second chamber diameter greater than or equal to said post diameter.

18. The strap connector assembly of claim 13 wherein said first chamber diameter is greater than said second chamber diameter.

19. The strap connector assembly of claim 15 wherein said first chamber diameter is greater than said head diameter.

20. The strap connector assembly of claim 13 wherein said retention post is mounted on an orthopedic brace component.

21. The strap connector assembly of claim 13 wherein said retention post is mounted on a strap retainer and a strap is engaged with said strap retainer.

22. The strap connector assembly of claim 13 wherein said body is mounted on an orthopedic brace component.

23. The strap connector assembly of claim 13 wherein said body is mounted on a strap retainer and a strap is engaged with said strap retainer.

24. The strap connector assembly of claim 13 wherein said body is substantially more flexible than said retention post.

25. A strap connector assembly for an orthopedic brace comprising:
   a retention post having a post diameter; and
   a body including a void segmented into a first chamber having a first chamber diameter and a second chamber having a second chamber diameter less than said first chamber diameter, said first and second chambers positioned adjacent one another to form a transition interface between said first and second chambers, said first chamber bounded at least in part by a sidewall and said second chamber bounded at least in part by a shelf extending inwardly relative to said sidewall, said shelf having an inner surface extending from a first retention tip at one end of said inner surface to a second retention tip at another end of said inner surface to bound said second chamber at least in part while providing a retention aperture at said transition interface, said retention aperture having a separation distance to form a restricted pathway between said first chamber and said second chamber, wherein said separation distance is less than said post diameter when said first or second or both retention tips are unstressed and is substantially equal to said post diameter when said first or second or both retention tips are stressed by said retention post and wherein said first chamber diameter and said second chamber diameter are greater than or equal to said post diameter.

26. The strap connector assembly of claim 25 further comprising a retention head positioned atop said retention post, said retention head having a head diameter greater than said post diameter.

27. The strap connector assembly of claim 26 wherein said second chamber diameter is less than said head diameter.

28. The strap connector assembly of claim 26 wherein said first chamber diameter is greater than said head diameter.

29. A strap connector assembly for an orthopedic brace comprising:
   an anchor mounted on a substantially rigid orthopedic brace component, said anchor including means for fixably mounting said anchor on said substantially rigid orthopedic brace component, a retention head having a head diameter, and a retention post having a post diameter less than said head diameter, wherein said retention head is positioned atop said retention post and said mounting means is positioned beneath said retention post; and
   a strap retainer substantially more flexible than said anchor and including a body and a strap loop member having a strap aperture extending through said strap loop member to receive and engage a strap, said body including a void segmented into a first chamber having a first chamber diameter and a second chamber having a second chamber diameter less than said first chamber diameter, said first and second chambers positioned adjacent one another to form a transition interface between said first and second chambers, said first chamber bounded at least in part by a sidewall and said second chamber bounded at least in part by a shelf extending inwardly relative to said sidewall, said shelf having an inner surface extending from a first retention tip at one end of said inner surface to a second retention tip at another end of said inner surface to bound said second chamber at least in part while providing a retention aperture at said transition interface, said retention aperture having a separation distance to form a restricted pathway between said first chamber and said second chamber, wherein said separation distance is less than said post diameter when said first or second or both retention tips are unstressed and is substantially equal to said post diameter when said first or second or both retention tips are stressed by said retention post and wherein said first chamber diameter is greater than or equal to said head diameter and said second chamber diameter is greater than or equal to said post diameter and less than said head diameter.

30. The strap connector assembly of claim 29 wherein said void is segmented into an upper chamber having an upper chamber diameter greater than or equal to said head diameter and a lower chamber positioned below said upper chamber, said lower chamber containing said second chamber and said first chamber.

31. The strap connector assembly of claim 29 wherein said substantially rigid orthopedic brace component is a knee brace cuff.

32. A method for connecting a strap to an orthopedic brace comprising:

providing a strap retainer including a strap loop member and a body having a void therein, said void segmented into a first chamber having a first chamber diameter and a second chamber having a second chamber diameter less than said first chamber diameter, said first and second chambers positioned adjacent one another to form a transition interface between said first and second chambers, said void having a retention aperture at said transition interface bounded by a first retention tip at a first end of said retention aperture and a second retention tip at a second end of said retention aperture, said first and second retention tips separated by a separation distance;

providing an anchor mounted on an orthopedic brace component, said anchor including means for fixably mounting said anchor on said orthopedic brace component, a retention head having a head diameter, and a retention post having a post diameter less than said head diameter, wherein said retention head is positioned atop said retention post and said mounting means is positioned beneath said retention post, and further wherein said separation distance is less than said post diameter when said first or second or both retention tips are unstressed and is substantially equal to said post diameter when said first or second or both retention tips are stressed by said retention post, and wherein said first chamber diameter is greater than or equal to said head diameter and said second chamber diameter is greater than or equal to said post diameter and less than said head diameter;

threading an end of a strap through a strap aperture formed through said strap loop member and selectively fixing the length of said strap at a desired strap adjustment;

aligning said first chamber with said retention head;

displacing said retention head in a first direction through said first chamber until said retention post is positioned in said first chamber;

displacing said retention post in a second direction toward said second chamber and into engagement with said first and second retention tips;

increasing said separation distance to substantially equal said post diameter by expansion flexion of said first or second or both retention tips in response to displacement of said retention post at said post diameter between said first and second retention tips; and decreasing said separation distance to less than said post diameter by elastic retraction of said first or second or both retention tips in response to continued displacement of said retention post after said post diameter between said first and second retention tips, thereby locking said retention post into said second chamber and connecting said strap to said orthopedic brace.

33. The method of claim 32 further comprising disconnecting said strap from said orthopedic brace by the steps of:

displacing said retention post in a third direction substantially opposite said second direction toward said first chamber and into engagement with said first and second retention tips;

increasing said separation distance to substantially equal said post diameter by expansion flexion of said first or second or both retention tips in response to displacement of said retention post at said post diameter between said first and second retention tips;

continuing displacement of said retention post after said post diameter between said first and second retention tips in said third direction until the entirety of said retention post is positioned in said first chamber; and displacing said retention head in a fourth direction substantially opposite said first direction until said retention head substantially clears said void, thereby withdrawing said retention post from said void and disconnecting said strap from said orthopedic brace without substantially modifying said desired strap adjustment.

34. A method for connecting a strap to an orthopedic brace comprising:

providing a strap retainer having a strap loop member and an anchor, said anchor including a retention head having a head diameter and a retention post having a post diameter less than said head diameter, wherein said retention head is positioned atop said retention post;

providing a body mounted on an orthopedic brace component, said body having a void therein, said void segmented into a first chamber having a first chamber diameter and a second chamber having a second chamber diameter less than said first chamber diameter, said first and second chambers positioned adjacent one another to form a transition interface between said first and second chambers, said first chamber bounded at least in part by a sidewall and said second chamber bounded at least in part by a shelf extending inwardly relative to said sidewall, said shelf having an inner surface extending from a first retention tip at one end of said inner surface to a second retention tip at another end of said inner surface to bound said second chamber at least in part while providing a retention aperture at said transition interface, said retention aperture having a separation distance to form a restricted pathway between said first chamber and said second chamber, wherein said separation distance is less than said post diameter when said first or second or both retention tips are unstressed and is substantially equal to said post diameter when said first or second or both retention tips are stressed by said retention post and wherein said first chamber diameter is greater than or equal to said head diameter and said second chamber diameter is greater than or equal to said post diameter and less than said head diameter;

threading an end of a strap through a strap aperture formed through said strap loop member and selectively fixing the length of said strap at a desired strap adjustment;

aligning said first chamber with said retention head;

displacing said retention head in a first direction through said first chamber until said retention post is positioned in said first chamber;

displacing said retention post in a second direction toward said second chamber and into engagement with said first and second retention tips;

increasing said separation distance to substantially equal said post diameter by expansion flexion of said first or second or both retention tips in response to displacement of said retention post at said post diameter between said first and second retention tips; and decreasing said separation distance to less than said post diameter by elastic retraction of said first or second or both retention tips in response to continued displacement of said retention post after said post diameter between said first and second retention tips, thereby locking said retention post into said second chamber and connecting said strap to said orthopedic brace.

35. The method of claim 34 further comprising disconnecting said strap from said orthopedic brace by the steps of:

displacing said retention post in a third direction substantially opposite said second direction toward said first chamber and into engagement with said first and second retention tips;

increasing said separation distance to substantially equal said post diameter by expansion flexion of said first or second or both retention tips in response to displacement of said retention post at said post diameter between said first and second retention tips;

continuing displacement of said retention post after said post diameter between said first and second retention tips in said third direction until the entirety of said retention post is positioned in said first chamber; and displacing said retention head in a fourth direction substantially opposite said first direction until said retention head substantially, clears said void, thereby withdrawing said retention post from said void and disconnecting said strap from said orthopedic brace without substantially modifying said desired strap adjustment.

36. A method for connecting a strap to an orthopedic brace comprising:

providing a body having a void therein, said void segmented into a first chamber having a first chamber diameter and a second chamber having a second chamber diameter less than said first chamber diameter, said first and second chambers positioned adjacent one another to form a transition interface between said first and second chambers, a retention aperture at said transition interface bounded by a first retention tip at a first end of said retention aperture and a second retention tip at a second end of said retention aperture, said first and second retention tips separated by a separation distance;

providing a retention post having a post diameter, wherein said separation distance is less than said post diameter when said first or second or both retention tips are unstressed and is substantially equal to said post diameter when said first or second or both retention tips are stressed by said retention post;

positioning said retention post is positioned in said first chamber;

displacing said retention post in a first direction toward said second chamber and into engagement with said first and second retention tips;

increasing said separation distance to substantially equal said post diameter by expansion flexion of said first or second or both retention tips in response to displacement of said retention post at said post diameter between said first and second retention tips; and decreasing said separation distance to less than said post diameter by elastic retraction of said first or second or both retention tips in response to continued displacement of said retention post after said post diameter between said first and second retention tips, thereby locking said retention post into said second chamber.

37. The method of claim 36 further comprising disconnecting said strap from said orthopedic brace by the steps of:

displacing said retention post in a second direction substantially opposite said first direction toward said first chamber and into engagement with said first and second retention tips;

increasing said separation distance to substantially equal said post diameter by expansion flexion of said first or second or both retention tips in response to displacement of said retention post at said post diameter between said first and second retention tips;

continuing displacement of said retention post after said post diameter between said first and second retention tips in said second direction until the entirety of said retention post is positioned in said first chamber; and withdrawing said retention post from said void.

38. A method for connecting a strap to an orthopedic brace comprising:

providing a strap retainer having a body, said body including a chamber having a retention aperture, said retention aperture having an aperture cross-sectional dimension and bounded at least in part by a flexible segment;

providing a retention post mounted on an orthopedic brace component, said retention post having a post cross-sectional dimension, wherein said aperture cross-sectional dimension is less than said post cross-sectional dimension when said flexible segment is unstressed and substantially equal to said post cross-sectional dimension when said flexible segment is stressed by said retention post;

engaging a strap with said strap retainer;

positioning said retention post in said chamber;

displacing said retention post in a first direction away from said chamber into engagement with said flexible segment;

increasing said aperture cross-sectional dimension to substantially equal said post cross-sectional dimension by expansion flexion of said flexible segment in response to displacement of said retention post at said post cross-sectional dimension through said retention aperture; and decreasing said aperture cross-sectional dimension to less than said post cross-sectional dimension by elastic retraction of said flexible segment in response to continued displacement of said retention post after said post cross-sectional dimension through said retention aperture, thereby resisting displacement of said retention post in a second direction toward said chamber by a displacement resistance and connecting said strap to said orthopedic brace.

39. The method of claim 38 further comprising disconnecting said strap from said orthopedic brace by the steps of:

displacing said retention post against said displacement resistance in said second direction into engagement with said flexible segment;

increasing said aperture cross-sectional dimension to substantially equal said post cross-sectional dimension by expansion flexion of said flexible segment in response to displacement of said retention post at said post cross-sectional dimension through said retention aperture;

continuing displacement of said retention post after said post cross-sectional dimension through said retention aperture; and withdrawing said retention post from said chamber.

40. A method for connecting a strap to an orthopedic brace comprising:

providing a body mounted on an orthopedic brace component, said body including a chamber having a retention aperture, said retention aperture having an aperture cross-sectional dimension and bounded at least in part by a flexible segment;

providing a strap retainer having a retention post, said retention post having a post cross-sectional dimension, wherein said aperture cross-sectional dimension is less than said post cross-sectional dimension when said flexible segment is unstressed and substantially equal to said post cross-sectional dimension when said flexible segment is stressed by said retention post;

engaging a strap with said strap retainer;

positioning said retention post in said chamber;

displacing said retention post in a first direction away from said chamber into engagement with said flexible segment;

increasing said aperture cross-sectional dimension to substantially equal said post cross-sectional dimension by expansion flexion of said flexible segment in response to displacement of said retention post at said post cross-sectional dimension through said retention aperture; and decreasing said aperture cross-sectional dimension to less than said post cross-sectional dimension by elastic retraction of said flexible segment in response to continued displacement of said retention post after said post cross-sectional dimension through said retention aperture, thereby providing a substantial resistance to displacement of said retention post in a second direction toward said chamber and connecting said strap to said orthopedic brace.

41. The method of claim 40 further comprising disconnecting said strap from said orthopedic brace by the steps of:

displacing said retention post in said second direction into engagement with said flexible segment by overcoming said substantial resistance;

increasing said aperture cross-sectional dimension to substantially equal said post cross-sectional dimension by expansion flexion of said flexible segment in response to displacement of said retention post at said post cross-sectional dimension through said retention aperture;

continuing displacement of said retention post alter said post cross-sectional dimension through said retention aperture; and withdrawing said retention post from said chamber.

* * * * *